United States Patent
Xiong

(10) Patent No.: US 10,653,753 B2
(45) Date of Patent: May 19, 2020

(54) TREATMENT OF HYPERINSULINEMIC HYPOGLYCEMIA WITH EXENDIN-4 DERIVATIVES

(71) Applicant: Eiger BioPharmaceuticals, Inc., Palo Alto, CA (US)

(72) Inventor: Xiaofeng Xiong, Palo Alto, CA (US)

(73) Assignee: Eiger Biopharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 16/081,578

(22) PCT Filed: Mar. 3, 2017

(86) PCT No.: PCT/US2017/020596
§ 371 (c)(1),
(2) Date: Aug. 31, 2018

(87) PCT Pub. No.: WO2017/152014
PCT Pub. Date: Sep. 8, 2017

(65) Prior Publication Data
US 2019/0060413 A1 Feb. 28, 2019

Related U.S. Application Data

(60) Provisional application No. 62/303,983, filed on Mar. 4, 2016.

(51) Int. Cl.
| | |
|---|---|
| *A61K 38/16* | (2006.01) |
| *A61P 11/00* | (2006.01) |
| *A61P 19/02* | (2006.01) |
| *A61K 38/26* | (2006.01) |
| *A61K 47/60* | (2017.01) |
| *A61P 3/10* | (2006.01) |
| *A61K 9/00* | (2006.01) |

(52) U.S. Cl.
CPC ............ *A61K 38/26* (2013.01); *A61K 9/0019* (2013.01); *A61K 47/60* (2017.08); *A61P 3/10* (2018.01)

(58) Field of Classification Search
None
See application file for complete search history.

(56) References Cited

U.S. PATENT DOCUMENTS

| | | | |
|---|---|---|---|
| 5,424,286 A | 6/1995 | Eng | |
| 6,469,021 B1 | 10/2002 | Truesdale et al. | |
| 6,573,291 B2 | 6/2003 | Gronberg et al. | |
| 6,903,074 B1 | 6/2005 | Morgan et al. | |
| 8,076,288 B2 | 12/2011 | Levy et al. | |
| 8,268,781 B2 | 9/2012 | Gotthardt et al. | |
| 9,616,108 B2 | 4/2017 | Stoffers et al. | |
| 9,821,031 B2 | 11/2017 | Stoffers et al. | |
| 10,188,702 B2 | 1/2019 | Stoffers et al. | |
| 2002/0123461 A1 | 9/2002 | Drucker et al. | |
| 2004/0092443 A1 | 5/2004 | Fridkin et al. | |
| 2004/0116331 A1* | 6/2004 | Seeley ............... A61K 38/26 514/10.8 |
| 2008/0269130 A1 | 10/2008 | Stoffers et al. | |
| 2010/0029554 A1 | 2/2010 | Ghosh et al. | |
| 2011/0124555 A1 | 5/2011 | Schmid | |
| 2015/0005233 A1 | 1/2015 | DeFrees | |
| 2015/0274800 A1 | 10/2015 | Schellenberger et al. | |
| 2015/0368311 A1 | 12/2015 | Sanofi | |
| 2016/0185837 A1 | 6/2016 | Bednarek et al. | |
| 2018/0117122 A1 | 5/2018 | McLaughlin et al. | |
| 2018/0147261 A1 | 5/2018 | McLaughlin et al. | |
| 2019/0336584 A1 | 11/2019 | Stoffers et al. | |

FOREIGN PATENT DOCUMENTS

| | | |
|---|---|---|
| WO | 02-081649 A2 | 10/2002 |
| WO | 2008-085982 A2 | 7/2008 |
| WO | 2016/191394 A1 | 12/2016 |
| WO | 2016/191395 A1 | 12/2016 |
| WO | 2018/094404 A1 | 5/2018 |

OTHER PUBLICATIONS

Kapoor et al., "Advances in the diagnosis and management of hyperinsulinemic hypoglycemia," Nature Clin. Pract. Endocrinol. Metab. 5:101-112 (2009) (Year: 2009).*
Kenny, "When hypoglycemia is not obvious: Diagnosing and treating under-recognized and undisclosed hypoglycemia," Primary Care Diabetes 8:3-11 (2014) (Year: 2014).*
Franco et al., "A Review of Studies Comparing Three Laparoscopic Procedures in Bariatric Surgery: Sleeve Gastrectomy, Roux-en-Y Gastric Bypass and Adjustable Gastric Banding," OBES SURG 21:1458-1468 (2011) (Year: 2011).*
International Search Report and Written Opinion received for International Patent Application No. PCT/US17/20596. dated May 26, 2017. 10 pages.
Manning, S. et al. "GLP-1: A Mediator of the Beneficial Metabolic Effects of Bariatrix Surgery?" *Physiology*, vol. 30, No. 1. Published Jan. 2015. 28 pages.
Montrose-Rafizadeh C. et al. "High Potency Antagonists of the Pancreatic Glucagon-like Peptide-1 Receptor." *The Journal of Biological Chemisty*, vol. 272, No. 32. Published Aug. 1997. 7 pages.
Salehi, M. et al. "Blockade of Glucagon-Like Peptide 1 Receptor Corrects Postprandial Hypoglycemia After Gastric Bypass." Gastroenterology, vol. 146, No. 3. Published Mar. 2014. 14 pages.

(Continued)

*Primary Examiner* — Julie Ha
*Assistant Examiner* — Kristina M Hellman
(74) *Attorney, Agent, or Firm* — Kilpatrick Townsend & Stockton LLP

(57) ABSTRACT

In one aspect, methods of treating hyperinsulinemic hypoglycemia comprising administration of an effective amount of a derivative of an exendin-4 peptide are provided. In some embodiments, the method comprises subcutaneously administering to a patient having hyperinsulinemic hypoglycemia a therapeutically effective amount of exendin(5-39).

17 Claims, No Drawings

(56) References Cited

OTHER PUBLICATIONS

ThanThan, S. et al. "Glucagon-Like Peptide-1 Inhibits Insulinotropic Effects of Oxyntomodulin and Glucagon in Cattle." *Domestic Animal Endocrinology*, vol. 42. Published Apr. 2012. pp. 155-164.

Willard, FS et al. "Small Molecule Allosteric Modulation of the Glucagon-Like Peptide-1 Receptor Enhances the Insulinotropic Effect of Oxyntomodulin." *Molecular Pharmacology*, vol. 28, No. 6. Published Aug. 2012. 8 pages.

"Amidation", The Free Dictionary, available at https://www.thefreedictionary.com/Amidation, retrieved online on Nov. 21, 2019, 3 pages.

Alexopoulos K., et al, "Design and Synthesis of Novel Biologically Active Thrombin Receptor Non-Peptide Mimetics Based on the Pharmacophoric Cluster Phe/Arg/NH2 of the Ser42-Phe-Leu-Leu-Arg46 Motif Sequence: Platelet Aggregation and Relaxant Activities" J Med. Chem. vol. 47, Issue 13, DOI:10.1021/jm031080v, Jun. 17, 2004, p. 3338-52.

Andreasen, J.J., et al., "Secretion of Glucagon-Like Peptide-1 and Reactive Hypoglycemia after Partial Gastrectomy". Digestion, 1994. 55(4): p. 221-228.

Andronati, S.A. et al, "Peptidomimetics—Antagonists of the Fibrinogen Receptors: Molecular Design, Structures, Properties and Therapeutic Applications." Curr Med Chem 11(9): 1183-211, 2004.

Ashkenazi A., et al.,"Immunoadhesins". Int. Rev. Immunol., vol. 10, Issue 2-3, DOI:10.3109/08830189309061697, 1993, p. 219-227.

Bantle, J.P., et al., "Hyperinsulinemic Hypoglycemia Developing Late after Gastric Bypass", Obes Surg. vol. 17, https://doi.org/10.1007/s11695-007-9102-6, May 2007, p. 592-595.

Botros, N., et al., "Effect of Carbohydrate Restriction in Patients with Hyperinsulinemic Hypoglycemia after Roux-en-Y Gastric Bypass", Obes Surg. vol. 24, Issue 11, https://doi.org/10.1007/s11695-014-1319-6,Jun. 6, 2014, p. 1850-1855.

Breslin, M.J., et al, "Non-Peptide alphavbeta3 Antagonists. Part 6: Design and Synthesis of alphavbeta3 Antagonists Containing a Pyridone or Pyrazinone Central Scaffold". Bioorg & Med Chem Lett vol. 13, Issue 10, DOI: 10.1016/S0960-894X(03)00254-3, Jun. 2003, p. 1809-12.

Buchwald, H., et al., "Long term, continuous intravenous heparin administration by an implantable infusion pump in ambulatory patients with recurrent venous thrombosis", Surgery, DOI:https://doi.org/10.5555/uri:pii:0039606080901257, vol. 88, Issue 4, Oct. 1, 1980, p. 507-516.

Calabria, A.C., et al., "Postoperative Surveillance and Detection of Postprandial Hypoglycemia after Fundoplasty in Children", published in final edited form as J Pediatr. vol. 159, No. 4, doi:10/1016/j.jpeds.2011.03.049,597-601. Oct. 2011, 11 pages.

Calabria, A.C., et al., "Postprandial Hypoglycemia in Children after Gastric Surgery: clinical characterization and pathophysiology", Horm Res Paediatr, vol. 85, No. 2, DOI:10.1159/000442155, 2016, p. 140-146.

Calabria, A.C., et al., "GLP-1 Receptor Antagonist Exendin-(9-39) Elevates Fasting Blood Glucose Levels in Congenital Hyperinsulinism Owing to Inactivating Mutations in the ATP-Sensitive K+ Channel" Diabetes, vol. 61, No. 10, DOI:10.2337/db12-0166, Oct. 2012, 2585-2591.

Cancelas, J., et al., "Suppression by Exendin(9-39)amide of Glucagon-Like Peptide-1 Insulinotropic Action in Rats Infused with Dimethyl Ester of Succinic Acid", Endocrine. vol. 15, Issue 3, DOI:10.1385/ENDO:15:3:283, Aug. 2001, p. 283-5.

Cancelas, J., et al., "Resistance of Succinic Acid Dimethyl Ester Insulinotropic Action to Exendin (9-39) Amide", Hormone and Metabolic Research, vol. 34, No. 1, DOI:10.1055/s-2002-19960, Feb. 1, 2002, pp. 13-15.

Caudy, A.A., et al. "Fragile X-related protein and VIG associate with the RNA interference machinery", Genes & Development vol. 16, No. 19, DOI:10.1101/gad.1025202, 2002, p. 2491-2496.

Cheon, H.G., et al., "High-affinity binding sites for related fibroblast growth factor ligands reside within different receptor immunoglobulin-like domains", Proceedings of the National Academy of Science, vol. 91, No. 3, DOI:10.1073/pnas.91.3.989, Feb. 1994, pp. 989-993.

Corywell, W., "Depressive Disorders", retrieved on Jun. 11, 2019 from https://www.merckmanuals.com/professional/psychiatric-disorders/mood-disorders/depressive-disorders, p. 1-10.

Cosgrove, K.E., et al., "BPDZ 154 Activates Adenosine 5'-Triphosphate-Sensitive Potassium Channels: *In Vitro* Studies Using Rodent Insulin-Secreting Cells and Islets Isolated from Patients with Hyperinsulinism", The Journal of Clinical Endocrinology and Metabolism, vol. 87, No. 11, DOI:https://doi.org/10.1210/jc.2002-020439, Nov. 1, 2002, 4860-4868.

Craig, C.M., et al. "Critical role for GLP-1 in symptomatic post-bariatric hypoglycaemia", Diabetologia, vol. 60, Issue 3, DOI:https://doi.org/10.1007/s00125-016-4179-x, Published in final edited form on Mar. 2017, p. 531-540.

Craig, C.M., et al., "Efficacy and pharmacokinetics of subcutaneous exendin (9-39) in patients with post-bariatric hypoglycaemia", Diabetes, Obesity and Metabolism, vol. 20, Issue 2, DOI:https://doi.org/10.1111/dom.13078, 2017, p. 1-10.

Davidson, M.B, et al., "Exenatide," Nature Reviews Drug Discovery, vol. 4, DOI:10.1038/nrd1828, Sep. 2005, p. 713-714.

De Leon, D.D., "Effect of Exendin-(9-38) on Glycemic Control in Subjects With Congenital Hyperinsulinism", retrieved on Nov. 21, 2019 from https://www.clinicaltrials.gov/ct2/show/NCT00571324, 28 pages.

De Leon, D.D., et al. "Exendin-(9-39) Corrects Fasting Hypoglycemia in SUR-1 / Mice by Lowering cAMP in Pancreatic beta-cells and Inhibiting Insulin Secretion" Journal of Biological Chemistry, vol. 283, Issue 38, DOI:10.1074/jbc.M804372200, Sep. 19, 2008, 24 pages.

De Leon, D.D., et al. "Role of Endogenous Glucagon-Like Peptide-1 in Islet Regeneration After Partial Pancreatectomy", Diabetes, vol. 52, DOI:https://doi.org/10.2337/diabetes.52.2.365, Feb. 2003, p. 365-371.

Deary, I.J., et al., "Partitioning the symptoms of hypoglycaemia using multi-sample confirmatory factor analysis", Diabetologia, vol. 35, Issue 8, DOI:https://doi.org/10.1007/BF00401150, 1993, p. 771-777.

Drucker, D.J., et al. "Biologic actions and therapeutic potential of the proglucagon-derived peptides", Nature Clinical Practice Endocrinology & Metabolism, vol. 1, No. 1, DOI:10.1038/ncpendmet0017, Nov. 2005, p. 22-31.

Dunne, M.J., et al. "Hyperinsulinism in Infancy: From Basic Science to Clinical Disease", Physiological Reviews, vol. 84, No. 1,DOI:10.1152/physrev.00022.2003, Jan. 2004, p. 239-275.

Edwards, C.M., et al. "Glucagon-like peptide 1 has a physiological role in the control of postprandial glucose in humans: studies with the antagonist exendin 9-39", Diabetes, vol. 48, No. 1, DOI:https://doi.org/10.2337/diabetes.48.1.86, Jan. 1999, p. 86-93.

Edwards, C.M., et al., "Subcutaneous glucagon-like peptide-1 (7-36) amide is insulinotropic and can cause hypoglycaemia in fasted healthy subjects", Clin Sci (Lond), vol. 95, No. 6, DOI:https://doi.org/10.1042/cs0950719, Dec. 1, 1998, p. 719-724.

Eisenberg, D., et al., "ASMBS Position Statement on Postprandial Hyperinsulinemic Hypoglycemia after Bariatric Surgery", Surgery for Obesity and Related Diseases, vol. 13, Issue 3, DOI:https://doi.org/10.1016/j.soard.2016.12.005, 2017, p. 371-378.

Eliasson, L., et al. "SUR1 Regulates PKA-independent cAMP-induced Granule Priming in Mouse Pancreatic B-Cells", J. Gen. Physiol, vol. 121, No. 3, DOI:10.1085/jgp.20028707, Mar. 2003, p. 181-197.

Eng, J., et al. "Isolation and Characterization of Exendin-4, an Exendin-3 Analogue, from Heloderma suspectum Venom: Further evidence for an exendin receptor on dispersed acini from guinea pig pancreas", The Journal of Biological Chemistry, vol. 267, No. 11, Apr. 15, 1992, p. 7402-7405.

Evan, G.I., et al., "Isolation of Monoclonal Antibodies Specific for Human c-myc Proto-Oncogene Product", Molecular and Cellular Biology, vol. 5, No. 12, Dec. 1985, p. 3610-3616.

Extended European Search Report dated, Nov. 28, 2018 in European Patent Application No. 16800620.3, 5 pages.

Extended European Search Report dated Aug. 30, 2011 in European Application No. 08713063.9, 5 pages.

Extended European Search Report dated Dec. 1, 2014 in European Application No. 14171762.9, 6 pages.

(56) References Cited

OTHER PUBLICATIONS

Extended European Search Report dated Jan. 21, 2019 in European Application No. 18201976.0, 6 pages.
Extended European Search Report, dated Mar. 9, 2018, European Patent Application No. 16800621.1, 4 pages.
Field, J., et al., "Purification of a RAS-responsive Adenylyl Cyclase Complex from Saccharomyces cerevisiae by Use of an Epitope Addition Method", Molecular and Cellular Biology, vol. 8, No. 5, DOI:10.1128/mcb.8.5.2159, May 1988, p. 2159-2165.
Final Office action dated Oct. 23, 2019 in U.S. Appl. No. 15/576,647, 12 pages.
Final Office action dated Sep. 25, 2019 in U.S. Appl. No. 15/576,647, 16 pages.
Fournet, J.C., et al., "Unbalanced Expression of 11p15 Imprinted Genes in Focal Forms of Congenital Hyperinsulinism", The Amercian Journal of Pathology, vol. 158, No. 6, Jun. 2001, DOI:https://doi.org/10.1016/S0002-9440(10)64689-5, p. 2177-2184.
Franco, J.V., et al., "A Review of Studies Comparing Three Laparoscopic Procedures in Bariatric Surgery: Sleeve Gastrectomy, Roux-en-Y Gastric Bypass and Adjustable Gastric Banding," OBES SURG, vol. 21, No. 9, DOI:10.1007/s11695-011-0390-5, 2011, p. 1458-1468.
Gebhard, B., et al., "Postprandial GLP-1, Norepinephrine, and Reactive Hypoglycemia in Dumping Syndrome", Digestive Diseases and Sciences, vol. 46, Issue 9, DOI:https://doi.org/10.1023/A:1010635131228, Sep. 2001, p. 1915-1923.
Goldfine, A.B., et al., "Patients with Neuroglycopenia after Gastric Bypass Surgery Have Exaggerated Incretin and Insulin Secretory Responses to a Mixed Meal", The Journal of Clinical Endocrinology & Metabolism, vol. 92, Issue 12, DOI:https://doi.org/10.1210/jc.2007-0918, Dec. 1, 2007, p. 4678-4685.
Goodson, J.M., Chapter 6 "Dental Applications" In: Medical Applications of Controlled Release, 1984, vol. 2, p. 116-138.
Gough, S.C.L, "Liraglutide: from clinical trials to clinical practice," Diabetes, Obesity and Metabolism, vol. 14, Issue 2, DOI:https://doi.org/10.1111/j.1463-1326.2012.01576.x, 2012, p. 33-40.
Heber, D., et al., "Endocrine and nutritional management of the post-bariatric surgery patient: an Endocrine Society Clinical Practice Guideline", J Clin Endocrinol Metab. vol. 95, Issue 11, DOI:10.1210/jc.2009-2128, Nov. 2010, p. 4823-4843.
Heidaran, M.A., et al., "Beta PDGFR-IgG chimera demonstrates that human beta PDGFR Ig-like domains 1 to 3 are sufficient for high affinity PDGF BB binding", The FASEB Journal, vol. 9, No. 1, DOI:https://doi.org/10.1096/fasebj.9.1.7821753, Jan. 1, 1995, p. 140-145.
Hepburn,D.A., et al., "Symptoms of acute insulin-induced hypoglycaemia in humans with and without IDDM", Diabetes Care, vol. 14, No. 11, DOI:https://doi.org/10.2337/diacare.14.11.949, Nov. 1991, p. 949-957.
Hofeldt, F.D., "Reactive hypoglycemia", Endocrinology and Metabolism Clinics of North America, vol. 18, No. 1, Mar. 1989, p. 185-201.
Hopp, T.P., et al., "A Short Polypeptide Marker Sequence Useful for Recombinant Protein Identification and Purification", Bio/Technology, vol. 6, No. 10, DOI:10.1038/nbt1088-1204, Oct. 1988, p. 1204-1210.
Hussain, K., et al., "Medications used in the treatment of hypoglycemia due to congenital hyperinsulinism of infancy (HI)", Pediatric Endocrinology Reviews, vol. 2, Supplement 1, Nov. 2004, p. 163-167.
International Hypoglycaemia Study Group (IHSG), AMIEL, S.A., et al., "Glucose concentrations of less than 3.0 mmol/L (54 mg/dL) should be reported in clinical trials: A joint position statement of the American Diabetes Association and the European Association for the Study of Diabetes", Diabetes Care, vol. 40, DOI:10.2337/dc16/2215, Jan. 2017, p. 155-157.
International Preliminary Report on Patentability dated May 21, 2019 in International Patent Application No. PCT/US2017/062838, 5 pages.
International Search Report and Written Opinion dated Aug. 18, 2016 in International Patent Application No. PCT/US2016/033837, 7 pages.
International Search Report and Written Opinion dated Aug. 19, 2016 in International Patent Application No. PCT/US2016/033836, 13 pages.
International Search Report and Written Opinion dated Jan. 23, 2018 in International Patent Application No. PCT/US2017/062838, 8 pages.
International Search Report and Written Opinion dated May 26, 2017 in International Patent Application No. PCT/US2017/020596, 10 pages.
International Search Report and Written Opinion dated Sep. 19, 2008 in International Patent Application No. PCT/US2008/000281, filed Jan. 8, 2008, 8 pages.
Kapoor, R.R., et al., "Advances in the diagnosis and management of hyperinsulininemic hypoglycemia," Nature Clinical Practice Endocrinology & Metabolism, vol. 5, No. 2, DOI:https://doi.org/10.1038/ncpendmet1046, Feb. 2009, p. 101-112.
Kellogg, T.A., et al., "Postgastric bypass hyperinsulinemic hypoglycemia syndrome: characterization and response to a modified diet", Surgery for Obesity and Related Diseases, vol. 4, Issue 4, DOI:10.1016/j.soard.2008.05.005, Jul.-Aug. 2008, p. 492-499.
Kenny, C., "When Hypoclycemia is not obvious: diagnosing and treating under-recognized and undisclosed hypoglycemia", Primary Care diabetes, vol. 8, Issue 1, DOI:http://dx.doi.org/10.1016/j.pcd.2013.09.002, Apr. 1, 2014, p. 3-11.
Kim, S.H., et al., "Glucose-stimulated insulin secretion in gastric bypass patients with hypoglycemic syndrome: no evidence for inappropriate pancreatic beta-cell function", Obesity Surgery, vol. 20, Issue 8, DOI:https://doi.org/10.1007/s11695-010-0183-2, Aug. 2010, p. 1110-1116.
Koh, T.H., et al., "Neonatal hypoglycaemia-the controversy regarding definition", Archives of Disease in Childhood, vol. 63, No. 11, DOI:10.1136/adc.63.11.1386, Nov. 1988, p. 1386-1388.
Kulkarni, R.N., et al., "Use of Exendin (9-39) Amide to define the in-vivo and in-vitro roles of GLP-1 (7-36) Amide in the regulation of Insulin secretion", Regulatory Peptides, vol. 57, No. 2, May 1995, p. 201.
Laferrere, B., et al., "Effect of weight loss by gastric bypass surgery versus hypocaloric diet on glucose and incretin levels in patients with type 2 diabetes", The Journal of Clinical Endocrinology & Metabolism, vol. 93, Issue 7, DOI:https://doi.org/10.1210/jc.2007-2851, Jul. 2008, p. 2479-2485.
Langa, K.M., et al., "The Diagnosis and Management of Mild Cognitive Impairment: A Clinical Review", JAMA,vol. 312, Issue 23, DOI:https://doi.org/10.1001/jama.2014.13806, Dec. 17, 2014, p. 2551-2561.
Langer, R., "New Methods of Drug Delivery", Science, vol. 249, Issue 4976, DOI:10.1126/science.2218494, Sep. 28, 1990, p. 1527-1533.
Larochelle, W.J., et al., "Specific Receptor Detection by a Functional Keratinocyte Growth Factor-Immunoglobulin Chimera", The Journal of Cell Biology, vol. 129, No. 2, DOI:https://doi.org/10.1083/jcb.129.2.357, Apr. 15, 1995, p. 357-366.
Larraufie, P., et al., "Important Role of the GLP-1 Axis for Glucose Homeostasis after Bariatric Surgery", Cell Reports, DOI:https://doi.org/10.1016/j.celrep.2019.01.047, vol. 26, Issue 6, Feb. 5, 2019, p. 1399-1408.
Lev-Ran, A., et al., "The diagnosis of postprandial hypoglycemia", Diabetes, vol. 30, Issue 12, DOI:10.2337/diab.30.12.996, Dec. 1981, p. 996-999.
Lutz-Freyermuth, C., et al., "Quantitative determination that one of two potential RNA-binding domains of the A protein component of the U1 small nuclear ribonucleoprotein complex binds with high affinity to stem-loop II of U1 RNA", Proceedings of the National Academy of Sciences of the United States of America, vol. 87, Issue 16, DOI:10.1073/pnas.87.16.6393, Aug. 1990, p. 6393-6397.
Mandal, A., "Defining Hypoglycemia", News Medical: Life Sciences, retrieved on Nov. 20, 2019 from https://www.news-medical.net/health/Defining-Hypoglycemia.aspx, 3 pages.

(56) References Cited

OTHER PUBLICATIONS

Manning, S., et al. "GLP-1: A Mediator of the Beneficial Metabolic Effects of Bariatric Surgery?", Physiology, vol. 30, Issue 1, DOI:https://doi.org/10.1152/physiol.00027.2014, Jan. 1, 2015, p. 50-62.

Martin, G.A., et al., "GAP domains responsible for ras p21-dependent inhibition of muscarinic atrial K+ channel currents", Science, vol. 255, Issue 5041, DOI:10.1126/science.1553544, Jan. 10, 1992, p. 192-194.

McLaughlin, T., et al. "Reversible Hyperinsulinemic Hypoglycemia after Gastric Bypass: A Consequence of Altered Nutrient Delivery", The Journal of Clinical Endocrinology & Metabolism, vol. 95, Issue 4, DOI:https://doi.org/10.1210/jc.2009-1628, Apr. 1, 2010, pp. 1851-1855.

Mechanick, J.I., et al., "Clinical practice guidelines for the perioperative nutritional, metabolic, and nonsurgical support of the bariatric surgery patient—2013 update: cosponsored by American Association of Clinical Endocrinologists", Obesity (Silver Spring), vol. 21, Issue 1, DOI:10.1002/oby.20461, Mar. 2013, 64 pages.

Meier et al., "Comment to: Patti ME, McMahon G, Mun EC et al. (2005) Severe hypoglycaemia post-gastric bypass requiring partial pancreatectomy: evidence for inappropriate insulin secretion and pancreatic islet hyperplasia. Diabetologia 49:2236-2240", Diabetologia, vol. 49, Issue 3, DOI:10.1007/s00125-005-0114-2, Mar. 2006, p. 607-608.

Meijeren, J.V., et al., "Evaluation of carbohydrate restriction as primary treatment for post-gastric bypass hypoglycemia", Surgery for Obesity and Related Diseases, vol. 13, Issue 3, DOI:https://doi.org/10.1016/j.soard.2016.11.004, Mar. 2017, p. 404-410.

Miholic, J., et al. "Emptying of the Gastric Substitute, Glucagon-like peptide-1 (GLP-1), and Reactive Hypoglycemia After Total Gastrectomy", Digestive Diseases and Sciences, vol. 36, No. 10, DOI:https://doi.org/10.1007/BF01296800, Oct. 1991, p. 1361-1370.

Moize, V.L., et al., "Nutritional pyramid for post-gastric bypass patients", Obesity Surgery, vol. 20, Issue 8, DOI:10.1007/s11695-010-0160-9, 2010, p. 1133-1141.

Montrose-Rafizadeh, C. et al. "High Potency Antagonists of the Pancreatic Glucagon-like Peptide-1 Receptor", The Journal of Biological Chemistry, vol. 272, Issue 34, DOI:10.1074/jbc.272.34.21201, Aug. 22, 1997, p. 21201-21206.

Myers, H.R., "Why Does Blood Pressure Drop After a Meal?", Livestrong.com, retrieved on Nov. 21, 2019, from http://www.livestrong.com/article/413792-postprandial-hypoglycemic-diet/, 2 pages.

Nabel, E.G., "Cardiovascular Disease", The New England Journal of Medicine, vol. 349, Issue 1, DOI:10.1056/NEJMra035098, Jul. 3, 2003, p. 60-72.

Naz, R.K, et al., "Novel human prostate-specific cDNA: molecular cloning, expression, and immunobiology of the recombinant protein", Biochemical and Biophysical Research Communications, vol. 297, Issue 5, DOI:https://doi.org/10.1016/S0006-291X(02)02349-5, Oct. 11, 2002, p. 1075-1084.

Ng, D.D., et al. 'Acarbose treatment of postprandial hypoglycemia in children after Nissen fundoplication', The Journal of Pediatrics, vol. 139, Issue 6, DOI:https://doi.org/10.1067/mpd.2001.119169, Dec. 2001, p. 877-879.

Nielsen, P.E., "Peptide nucleic acids as therapeutic agents", Current Opinion in Structural Biology, vol. 9, Issue 3, DOI: https://doi.org/10.1016/S0959-440X(99)80047-5, Jun. 1999, p. 353-357.

Non-Final Office action dated Mar. 21, 2019 in U.S. Appl. No. 15/576,647, 17 pages.

Office Action dated Feb. 22, 2019 in European Patent Application No. 16800621.1, 3 pages.

Paborsky, L.R., et al., "Mammalian cell transient expression of tissue factor for the production of antigen", Protein Engineering, Design and Selection, vol. 3, Issue 6, DOI:https://doi.org/10.1093/protein/3.6.547, May 1990, p. 547-553.

Palladino, A.A., et al., "Hyperinsulinism in Infancy and Childhood: When an Insulin Level is Not Always Enough", Clinical Chemistry, vol. 54, Issue 2, DOI:10.1373/clinchem.2007.098988, Jan. 2008, p. 256-263.

Palladino, A.A., et al., "Increased Glucagon-Like Peptide-1 secretion and Postprandial Hypoglycemia in Children after Nissen Fundoplication", The Journal of Clinical Endocrinology & Metabolism, vol. 94, Issue 1, DOI:10.1210/jc.2008-1263, Jan. 2009, p. 39-44.

Patti, M., et al., "Hypoglycemia after Gastric Bypass: The Dark Side of GLP-1", Gastroentrology, vol. 146, Issue 3, DOI:10.1053/j.gastro.2014.01.038, Mar. 2014, p. 605-608.

Patti, M.E., et al., "Severe hypoglycemia postgastric bypass requiring partial pancreatectomy: evidence for inappropriate insulin secretion and pancreatic islet hyperplasia", Diabetologia, vol. 48, Issue 11, DOI:10.1007/500125-005-1933-x , 2005, p. 2236-2240.

Pramanick, S., et al., "Excipient Selection in Parenteral Formulation Development", Pharma Times, vol. 45, No. 3, Mar. 2013, p. 65-77.

Salehi, M., et al., "Blockade of Glucagon-like Peptide 1 Receptor Corrects Postprandial Hypoglycemia After Gastric Bypass", Gastroenterology, vol. 146, Issue 3, DOI:https://doi.org/10.1053/j.gastro.2013.11.044, Mar. 2014, p. 669-680.

Salehi, M., et al., "Gastric Bypass Surgery Enhances Glucagon-Like Peptide 1-Stimulated Postprandial Insulin Secretion in Humans", Diabetes, vol. 60, Issue 9, DOI:https://doi.org/10.2337/db11-0203, Sep. 2011, p. 2308-2314.

Saudek, C.D., et al., "A Preliminary Trial of the Programmable Implantable Medication System for Insulin Delivery", The New England Journal of Medicine, vol. 321, No. 9, DOI: 10.1056/NEJM198908313210904, Aug. 31, 1989, p. 574-579.

Schirra, J., et al., "Endogenous glucagon-like peptide 1 controls endocrine pancreatic secretion and antro-pyloro-duodenal motility in humans", Gut, vol. 55, Issue 2, DOI:10.1136/gut.2004.059741, Feb. 2006, p. 243-251.

Schirra, J., et al., "Exendin(9-39)amide Is an Antagonist of Glucagon-like Peptide-1(7-36)amide in Humans", The Journal of Clinical Investigation, vol. 101, No. 7, DOI:https://doi.org/10.1172/JCI1349, Apr. 1, 1998, p. 1421-1430.

Scroochi, L.A., et al., "Glucose intolerance but normal satiety in mice with a null mutation in the glucagon-like peptide 1 receptor gene", Nature Medicine, vol. 2, No. 11, DOI:https://doi.org/10.1038/nm1196-1254, Nov. 1, 1996, p. 1254-1258.

Seaquist, E.R., et al., "Hypoglycemia and Diabetes: A Report of a Workgroup of the American Diabetes Association and The Endocrine Society", Diabetes Care, vol. 36, Issue 5, DOI:https://doi.org/10.2337/dc12-2480 , May 2013, p. 1384-1395.

Seghers, V., et al. "Sur 1 Knockout Mice. A Model for KATP Channel-Independent Regulation of Insulin Secretion", The Journal of Biological Chemistry, vol. 275, No. 13, DOI:10.1074/jbc.275.13.9270, Mar. 31, 2000, p. 9270-9277.

Sefton, M.V., "Implantable Pumps" Critical Reviews in Biomedical Engineering, vol. 14, Issue 3 , p. 201-240.

Service, F.J., et al., "Mean Amplitude of Glycemic Excursions, a Measure of Diabetic Instability", Diabetes, vol. 19, Issue 9, DOI:https://doi.org/10.2337/diab.19.9.644, Sep. 1970, p. 644-655.

Service, G.J., et al., "Hyperinsulinemic hypoglycemia with nesidioblastosis after gastric-bypass surgery", The New England Journal of Medicine, vol. 353, Issue 3, DOI:10.1056/NEJMoa043690, Jul. 21, 2005, p. 249-254.

Skinner, R.H., et al., "Use of the Glu-Glu-Phe C-terminal Epitope for Rapid Purification of the Catalytic Domain of Normal and Mutant ras GTPase-activating Proteins", The Journal of Biological Chemistry, vol. 266, No. 22, Issue of Aug. 5, 1991, p. 14163-14166.

Song, J., et al, "NMR for the design of functional mimetics of protein-protein interactions: one key is in the building of bridges", Biochemistry and Cell Biology, vol. 76, Issue 2-3, DOI:10.1139/bcb-76-2-3-177, 1998, p. 177-188.

Stanley, C.A., et al., "Editorial: Advances in Diagnosis and Treatment of Hyperinsulinism in Infants and Children", The Journal of Clinical Endocrinology & Metabolism, vol. 87, Issue 11, DOI:10.1210/jc.2002-021403, Nov. 2002, p. 4857-4859.

Suhl, E., et al., "Medical nutrition therapy for post-bariatric hypoglycemia: practical insights", Surgery for Obesity and Related Diseases, vol. 13, Issue 5, DOI:10.1016/j.soard.2017.01.025, May 2017, p. 888-896.

Tack, J., et al., "Pathophysiology, diagnosis and management of postoperative dumping syndrome", Nature Reviews Gastroenterol-

(56) References Cited

OTHER PUBLICATIONS ogy & Hepatology, vol. 6, Issue 10, DOI:https://doi.org/10.1038/nrgastro.2009.148, Sep. 1, 2009, p. 583-590.

Tan, M.J., et al., "Repeat subcutaneous dosing of exendin 9-39 reduces hyperinsulinemic hypoglycemia and neuroglycopenic symptoms in patients with post-bariatric hypoglycemia", Poster presentation at the American Diabetes Association's 77th Scientific Sessions, San Diego, CA, Jun. 9-13, 2017, 1 page.

Thanthan, S., et al., "Glucagon-like peptide-1 inhibits insulinotropic effects of oxyntomodulin and glucagon in cattle", Domestic Animal Endocrinology, vol. 42, Issue 3, DOI:https://doi.org/10.1016/j.domaniend.2011.11.004, Apr. 2012, p. 155-164.

Todd, J.F., et al., "A tumor that secretes glucagon-like peptide-1 and somatostatin in a patient with reactive hypoglycemia and diabetes", The Lancet, vol. 361, Issue 9353, DOI:https://doi.org/10.1016/S0140-6736(03)12256-8, Jan. 18, 2003, p. 228-230.

Toft-Nielsen, M., et al., "Exaggerated secretion of glucagon-like peptide-1 (GLP-1) could cause reactive hypoglycaemia", Diabetologia, vol. 41, Issue 10, DOI:https://doi.org/10.1007/s001250051049, 1998, p. 1180-1186.

Toft-Nielsen, M.-B., et al., "Determinants of the Effectiveness of Glucagon-Like Peptide-1 in Type 2 Diabetes", The Journal of Clinical Endocrinology & Metabolism, vol. 86, Issue 8, DOI:https://doi.org/10.1210/jcem.86.8.7743, Aug. 1, 2001, p. 3853-3860.

Traina, A.N., et al., "Primer on Pramlintide, an Amylin Analog", The Diabetes Educator, vol. 37, Issue 3, DOI:10.1177/0145721711403011, May/Jun. 2011, p. 426-431.

Vilsboll T., et al., No reactive hypoglycaemia in Type 2 diabetic patients after subcutaneous administration of GLP-1 and intravenous glucose Diabetic Medicine, vol. 18, Issue 2, DOI:https://doi.org/10.1046/j.1464-5491.2001.00424.x, Dec. 20, 2001, p. 144-149.

Vogt, A., et al, "A Non-peptide Mimetic of Ras-CAAX: selective Inhibition of Farnesyltransferase and Ras Processing", The Journal of Biological Chemistry, vol. 270, No. 2, DOI:https://doi.org/10.1074/jbc.270.2.660, Issue of Jan. 13, 1995, pp. 660-664.

Webb, M., et al., "Growth restriction and exendin 4 promote endocrine expression in cultured islet cells derived from patients with persistent hyperinsulinemic hypoglycemia of infancy (PHHI)", Endocrine Research, vol. 31, Issue 2, DOI:10.1080/07435800500229235, 2005, p. 99-109.

Williard, F.S., et al., "Small Molecule Allosteric Modulation of the Glucagon-Like Peptide-1 Recetor Enhances the Insulinotropic Effect of Oxyntomodulin", Molecular Pharmacology, vol. 82, Issue 6, DOI:https://doi.org/10.1124/mol.112.080432, 2012, p. 1066-1073.

Lee, et al. "OR20-5 28-Day Dosing with Avexitide Improves Hyperinsulinemic Hypoglycemia in Patients with Severe, Refractory Post-Bariatric Hypoglycemia: The Prevent Study", Journal of the Endocrine Society, vol. 3, Issue Supplement 1, DOI:10.1210/js.2019-OR20-5, Apr. 30, 2019, pp. 1-5.

International Search Report and Written Opinion dated Jan. 15, 2020 in International Patent Application No. PCT/US2019/056278, 26 pages.

\* cited by examiner

TREATMENT OF HYPERINSULINEMIC HYPOGLYCEMIA WITH EXENDIN-4 DERIVATIVES

CROSS-REFERENCE TO RELATED APPLICATIONS

This application is a national stage application under 35 U.S.C. § 371 of International Application No. PCT/US2017/020596, filed Mar. 3, 2017, which claims priority to U.S. Provisional Application No. 62/303,983, filed Mar. 4, 2016, the entire content of each of which is incorporated by reference herein.

SEQUENCE LISTING

The instant application contains a Sequence Listing which has been filed electronically in ASCII format and is hereby incorporated by reference in its entirety. Said ASCII copy, created on Oct. 4, 2019, is named SequenceListing_1097894.txt and is 2,993 bytes in size.

FIELD OF INVENTION

The present invention provides methods and compositions for the treatment of hypoglycemia, particularly post-bariatric hyperinsulinemia and more generally hyperinsulinemic hypoglycemia of any origin, and so relates to the fields of biology, chemistry, medicinal chemistry, medicine, molecular biology, and pharmacology.

BACKGROUND OF THE INVENTION

Roux-en-Y gastric bypass (RYGB) is a form of bariatric surgery that is widely performed for medically complicated obesity and that cures type 2 diabetes in 85% of cases. The physiologic mechanisms mediating diabetes resolution are controversial, but it is believed that the incretin hormone glucagon-like peptide-1 (GLP-1) may play an important role. GLP-1 stimulates the secretion of insulin by pancreatic beta cells and is responsible for the "incretin" effect: incretin hormones enhance the glucose-dependent secretion of insulin, such that pancreatic beta cells will secrete more insulin after an oral glucose load than after an isoglycemic IV glucose load. Enhanced secretion of GLP-1 after RYGB, and a resultant elevation in insulin secretion, may play a primary role in the resolution of diabetes after RYGB.

However, as the use of bariatric surgical procedures continues to increase worldwide, a severe complication—hyperinsulinemic hypoglycemia—is increasingly reported. This disorder manifests in 1-6% of RYGB patients, and leads to severe symptomatic hypoglycemia, often multiple times daily, characterized by glucose concentrations low enough (20-40 mg/dL) to cause seizures, altered mental status, loss of consciousness, cognitive dysfunction, disability, and death. Quality of life is severely diminished, and many patients cannot care for themselves or others, work, drive, or be left unaccompanied. Currently there is no satisfactory treatment for hyperinsulinemic hypoglycemia. Severe cases have been managed with near-total to total pancreatectomy, which results in insulin-dependent diabetes and is associated with a 6% surgical mortality risk. There continues to be a need for a therapy that safely and effectively mitigates hyperinsulinemic hypoglycemia.

BRIEF SUMMARY OF THE INVENTION

In one aspect, methods of preventing or treating hyperinsulinemic hypoglycemia or associated acute or chronic symptoms or outcomes thereof are provided. In some embodiments, the method comprises administering an exendin-4 derivative to a patient in need thereof, wherein the exendin-4 derivative is selected from the group consisting of exendin(3-39), exendin(4-39), exendin(5-39), exendin(6-39), exendin(7-39), and exendin(8-39).

In some embodiments, the exendin-4 derivative is pegylated (e.g., pegylated exendin(3-39), pegylated exendin(4-39), pegylated exendin(5-39), pegylated exendin(6-39), pegylated exendin(7-39), or pegylated exendin(8-39)). In some embodiments, the exendin-4 derivative is pegylated exendin(5-39). In some embodiments, the exendin-4 derivative is not pegylated.

In some embodiments, the exendin-4 derivative is subcutaneously administered. In some embodiments, the exendin-4 derivative is subcutaneously administered as an immediate release formulation. In some embodiments, the exendin-4 derivative is subcutaneously administered as an extended release formulation.

In some embodiments, the patient has previously had gastrointestinal surgery. In some embodiments, the patient has previously had bariatric surgery. In some embodiments, the patient has previously had a non-bariatric gastrointestinal surgical procedure. In some embodiments, the patient has congenital hyperinsulinemic hypoglycemia.

In some embodiments, the exendin-4 derivative is administered (e.g., subcutaneously administered) at a dose of about 0.01 mg to about 50 mg. In some embodiments, the exendin-4 derivative is administered (e.g., subcutaneously administered) at a dose in the range of 0.01 mg to 1 mg, e.g., about 0.01 mg to about 10 mg, about 0.5 mg to about 30 mg, about 0.5 mg to about 20 mg, or about 0.5 mg to about 10 mg. In some embodiments, the exendin-4 derivative is administered at a dose in the range of 0.1 mg to 1 mg. In some embodiments, the exendin-4 derivative is administered (e.g., subcutaneously administered) once per day (QD) or twice per day (BID). In some embodiments, the exendin-4 derivative is administered (e.g., subcutaneously administered) once per week (QW) or twice per week (BIW). In some embodiments, the exendin-4 derivative is administered at a total daily dose of about 0.01 mg to about 50 mg, e.g., about 0.5 mg to about 30 mg, about 0.5 mg to about 20 mg, or about 0.5 mg to about 10 mg.

In some embodiments, the exendin-4 derivative is a non-pegylated exendin-4 derivative and the non-pegylated exendin-4 derivative is administered at a dose in the range of about 0.5 mg to about 30 mg. In some embodiments, the non-pegylated exendin-4 derivative is administered QD or BID. In some embodiments, the exendin-4 derivative is a non-pegylated exendin-4 derivative and the non-pegylated exendin-4 derivative is administered at a dose in the range of about 0.5 mg to about 30 mg BID (e.g., about 0.5 mg to about 20 mg BID, about 0.5 mg to about 15 mg BID, or about 0.5 mg to about 10 mg BID). In some embodiments, the exendin-4 derivative is exendin(5-39) and the exendin(5-39) is administered (e.g., subcutaneously administered) at a dose in the range of about 0.5 mg to about 30 mg BID (e.g., about 0.5 mg to about 20 mg BID, about 0.5 mg to about 15 mg BID, or about 0.5 mg to about 10 mg BID).

In some embodiments, the exendin-4 derivative is a pegylated exendin-4 derivative and the pegylated exendin-4 derivative is administered at a dose in the range of about 0.5 mg to about 30 mg. In some embodiments, the non-pegylated exendin-4 derivative is administered QW or BIW. In some embodiments, the exendin-4 derivative is a pegylated exendin-4 derivative and the pegylated exendin-4 derivative is administered at a dose in the range of 0.5 mg to 30 mg once per week (QW) or twice per week (BIW) (e.g., about 0.5 mg to about 20 mg BID, about 0.5 mg to about 15 mg BID, or about 0.5 mg to about 10 mg QW or BIW). In some embodiments, the exendin-4 derivative is pegylated exendin (5-39) and the pegylated exendin(5-39) is administered at a dose in the range of about 0.5 mg to about 30 mg QW or BIW (e.g., about 0.5 mg to about 20 mg BID, about 0.5 mg to about 15 mg BID, or about 0.5 mg to about 10 mg QW or BIW).

In some embodiments, the exendin-4 derivative is a non-pegylated exendin-4 derivative and the non-pegylated exendin-4 derivative is administered at a dose in the range of about 0.01 mg to about 10 mg. In some embodiments, the non-pegylated exendin-4 derivative is administered QD or BID. In some embodiments, the exendin-4 derivative is a non-pegylated exendin-4 derivative and the non-pegylated exendin-4 derivative is administered at a dose in the range of 0.1 mg to 1 mg BID. In some embodiments, the exendin-4 derivative is exendin(5-39) and the exendin(5-39) is administered (e.g., subcutaneously administered) at a dose in the range of 0.1 mg to 1 mg BID.

In some embodiments, the exendin-4 derivative is a pegylated exendin-4 derivative and the pegylated exendin-4 derivative is administered at a dose in the range of about 0.01 mg to about 10 mg. In some embodiments, the non-pegylated exendin-4 derivative is administered QW or BIW. In some embodiments, the exendin-4 derivative is a pegylated exendin-4 derivative and the pegylated exendin-4 derivative is administered at a dose in the range of 0.1 mg to 1 mg once per week (QW) or twice per week (BIW). In some embodiments, the exendin-4 derivative is pegylated exendin(5-39) and the pegylated exendin(5-39) is administered at a dose in the range of 0.1 mg to 1 mg QW or BIW.

These and other aspects and embodiments of the invention are described in more detail below.

DETAILED DESCRIPTION OF THE INVENTION

I. Introduction

In one aspect, the present invention relates to exendin-4 derivatives that act as an antagonist of the GLP-1 receptor. Exendin-4, a 39-amino acid peptide, is a hormone that was originally isolated from Gila monster venom and which is a GLP-1 receptor agonist. N-terminal truncation of exendin-4 by 8 amino acids resulted in a GLP-1 receptor antagonist, exendin(9-39). See, Montrose-Rafizadeh et al., *Journal of Biological Chemistry*, 272:21201-21206 (1997).

As described herein, shorter deletions of N-terminal amino acids from exendin-4 are expected to retain antagonistic activity for the GLP-1 receptor, or even show improved antagonistic activity for the GLP-1 receptor, as compared to exendin(9-39). In some embodiments, the exendin-4 derivative comprising an N-terminal deletion is selected from the group consisting of exendin(3-39), exendin(4-39), exendin(5-39), exendin(6-39), exendin(7-39), and exendin(8-39). In some embodiments, a pegylated or unpegylated form of exendin(3-39), exendin(4-39), exendin (5-39), exendin(6-39), exendin(7-39), or exendin(8-39) exhibits improved antagonistic activity without agonistic activity for the GLP-1 receptor as compared to exendin(9-39). Thus, in some embodiments, a lower dose and/or less frequent dosing can be used for an exendin-4 derivative as described herein as compared to dosing regimens that are used for exendin(9-39).

II. Definitions

The terminology used herein is for the purpose of describing particular embodiments only, and is not intended to be limiting, because the scope of the present invention will be limited only by the appended claims. Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings unless a contrary intention is apparent. In some cases, terms with commonly understood meanings are defined herein for clarity and/or for ready reference, and the inclusion of such definitions herein should not be construed as representing a substantial difference over the definition of the term as generally understood in the art.

Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

All numerical designations, e.g., pH, temperature, time, concentration, and molecular weight, including ranges, are approximations which are varied (+) or (−) by increments of 0.1 or 1.0, as appropriate. It is to be understood, although not always explicitly stated that all numerical designations are preceded by the term "about."

The singular forms "a," "an," and "the" include plural referents unless the context clearly dictates otherwise. Thus, for example, reference to "a compound" includes a plurality of compounds.

The terms "administer," "administering," and "administration" refer to introducing a compound, a composition, or an agent of the present disclosure into a subject, such as a human. In the context of the present invention, one preferred route of administration of the agents is subcutaneous administration. Other routes are intravenous administration and oral administration.

The term "comprising" is intended to mean that the compounds, compositions and methods include the recited elements, but does not exclude others. "Consisting essentially of" when used to define compounds, compositions and methods, shall mean excluding other elements that would materially affect the basic and novel characteristics of the claimed invention. Embodiments defined by each of these transition terms are within the scope of this invention.

As used herein, the terms "patient" and "subject" interchangeably refer to an individual (e.g., a human or a non-human mammal) having or prone to having a condition that can be treated or prevented by administration of an exendin-4 derivative as described herein. In some embodiments, a patient or subject has hyperinsulinemic hypoglycemia. In some embodiments, a patient or subject has previously had a bariatric procedure (e.g., gastric bypass surgery).

The term "pharmaceutical composition" is meant to encompass a composition suitable for administration to a subject. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intratracheal, intramuscular, subcutaneous, inhalational, and the like.

The terms "QD" and "BID" have their usual meanings of, respectively, administration of a composition (e.g., a composition comprising an exendin-4 derivative as described herein) once per day or twice per day. In some embodiments, administration once per day (QD) means that at least 20 hours, at least 22 hours, or about 24 hours elapse between administrations. In some embodiments, administration once per day means administration about every 24 hours. In some embodiments, administration twice per day (BID) means that at least 6 hours, at least 8 hours, at least 10 hours, at least 11 hours, or about 12 hours elapse between administrations. In some embodiments, administration twice per day means administration about every 12 hours.

The terms "QW" and "BIW" have their usual meanings of, respectively, administration of a composition (e.g., a composition comprising an exendin-4 derivative as described herein) once per week or twice per week. In some embodiments, administration once per week (QW) means that at least 5 days, at least 6 days, or about 7 days elapse between administrations. In some embodiments, administration once per day means administration about every 7 days. In some embodiments, administration twice per week (BIW) means that at least 2 days, about 3 days, or about 4 days elapse between administrations. In some embodiments, administration once per day means administration two times in a 7-day period (e.g., on days 1 and 4 of a 7-day period).

The term "therapeutically effective amount" as used herein refers to that amount of a compound, agent, or drug (e.g., an exendin-4 derivative as disclosed herein) being administered that will treat to some extent a disease, disorder, or condition, e.g., relieve one or more of the symptoms of the disease, i.e., infection, being treated, and/or that amount that will prevent, to some extent, one or more of the symptoms of the disease that the subject being treated has or is at risk of developing.

The terms "treatment," "treating," or "treat," as used herein in reference to administering an exendin-4 derivative to treat hyperinsulinemic hypoglycemia, covers any treatment of the disease in a human subject, and includes: (a) reducing the risk, frequency, or severity of hypoglycemic episodes in patients with a history of hyperinsulinemic hypoglycemia; (b) reducing the risk of occurrence of hypoglycemia in a subject determined to be predisposed to the disease, such as a person who has received post-bariatric surgery, but not yet diagnosed as having the disease; (c) impeding the development of the disease; and/or (d) relieving the disease, i.e., causing regression of the disease and/or relieving one or more disease symptoms.

III. Methods for the Treatment of Hyperinsulinemic Hypoglycemia

In one aspect, methods for the treatment and prevention of hyperinsulinemic hypoglycemia or associated acute or chronic symptoms or outcomes thereof are provided. In some embodiments, the method comprises the subcutaneous administration of a GLP-1 receptor antagonist that is an exendin-4 derivative to a patient in need thereof. In some embodiments, the exendin-4 derivative that is subcutaneously delivered is exendin(3-39), exendin(4-39), exendin(5-39), exendin(6-39), exendin(7-39), or exendin(8-39). In some embodiments, the exendin-4 derivative that is subcutaneously delivered is a pegylated form of exendin(3-39), exendin(4-39), exendin(5-39), exendin(6-39), exendin(7-39), or exendin(8-39). In some embodiments, a patient in need thereof is a patient having hyperinsulinemic hypoglycemia post bariatric surgery. In some embodiments, a patient in need thereof is a patient having hyperinsulinemic hypoglycemia post gastrointestinal surgery (e.g., post non-bariatric gastrointestinal surgery). In some embodiments, a patient in need thereof is a patient having congenital hyperinsulinemic hypoglycemia.

Patient Population

In some embodiments, a patient to be treated is a patient having hyperinsulinemic hypoglycemia. "Hyperinsulinemic hypoglycemia," as used herein, encompasses the conditions dumping syndrome, nesideoblastosis, noninsulinoma pancreatogenous hypoglycemia syndrome (NIPHS), and/or post-prandial reactive hypoglycemia. Hyperinsulinemic hypoglycemia may result from a gastric or bariatric procedure, or may have a congenital, acquired, or induced origin.

In some embodiments, a patient to be treated has previously had a bariatric and/or related metabolic procedure, such as but not limited to Roux-en-Y Gastric Bypass. Bariatric and/or related metabolic procedures include, but are not limited to, Roux-en-Y Gastric Bypass, Vertical Sleeve Gastrectomy, placement of an endosleeve device, such as the EndoBarrier Gastrointestinal Liner System, also called an "endoluminal liner," duodenal mucosal resurfacing, also referred to as duodenal ablation, partial bypass of the duodenum, involving duodeno-ileal or duodeno-jejunal anastomosis, vagal nerve blockade, and/or pyloroplasty.

A bariatric procedure (i.e., bariatric surgery) typically involves any of the foregoing: partially or completely bypassing the duodenum and/or decreasing nutrient exposure to the duodenum, increasing the rapidity of nutrient transit to the lower part of the intestines (often specifically the ileum), and/or otherwise increasing ileal nutrient exposure. Bariatric surgery may be intended for weight loss or metabolic benefit (such as resolution of diabetes), or both. Such weight loss or metabolic procedures, referred to herein as "bariatric procedures" may enhance secretion of GLP-1 from the distal small intestine, especially the ileum, leading to elevated insulin secretion, and in some patients hypoglycemia. The patient may be referred to as a "post bariatric surgery" patient or "post-RYGB." In a preferred embodiment, the patient has had bariatric surgery to aid in weight loss and/or metabolic control and has suffered hypoglycemic excursions requiring urgent medical attention.

In some embodiments, the patient treated has previously had a non-bariatric surgical procedure involving the gastrointestinal system (including but not limited to esophagectomy, for example for treatment of esophageal cancer, Nissen fundoplication, for example gastroesophageal reflux, or gastrectomy, for example for treatment of gastric cancer) and so may be referred to herein as "post gastrointestinal surgery."

In some embodiments, the patient treated is prediabetic and/or insulin resistant and may benefit from prevention of pancreatic hyperstimulation from oral carbohydrate ingestion leading to post-prandial hypoglycemia. In some embodiments, a treated patient has a congenital, acquired, or induced form of hyperinsulinemic hypoglycemia, such as congenital hyperinsulinism or sometimes referred to as congenital nesidioblastosis. Acquired hyperinsulinism may result from insulinomas, autoimmune syndromes, reactive hypoglycemia, adult nesidioblastosis, or gastric dumping syndrome (not due to bariatric or GI surgery). Congenital hyperinsulinism may manifest in the newborn period, or many years later. Accordingly, the compositions and methods disclosed herein encompass the treatment of such conditions.

In some embodiments, the patient is an adult patient with hyperinsulinemic hypoglycemia. In some embodiments, a patient is diagnosed as having hyperinsulinemic hypoglycemia according to the diagnostic criteria described in De Leon and Stanley, *Best Proct Res Clin Endocrinol Metab*, 2013, 27:763-769, which is incorporated by reference herein. A typical adult patient with hyperinsulinemic hypoglycemia will present within 10 years of bariatric and/or other gastrointestinal surgery with one or more symptoms of hypoglycemia (e.g. palpitations, tremor, weakness, sweating, confusion, fatigue, blurred vision,) within 5 hours of eating that are associated with a plasma glucose of ≤60 mg/dL and immediate resolution with carbohydrate intake. In some embodiments, the patient exhibits one or more neuroglycopenic symptoms, such as altered mental status, loss of consciousness, or seizures. Hyperinsulinemia (>2 μU/mL or 13.9 pmol/L) may be documented in the proper laboratory setting at the time of the hypoglycemic event. However, documentation of hyperinsulinemia is not always possible due to logistical challenges associated with this testing (which involves induced hypoglycemia) and concerns over patient safety.

With the increasing incidence of obesity in children and adolescents, and the consequent increasing use of bariatric surgery in the pediatric and adolescent population, hyperinsulinemic hypoglycemia is anticipated in this cohort, and will likely present similarly to the typical adult patient. Thus, in some embodiments, the compositions and methods disclosed herein encompass the treatment of such patients.

Exendin-4 Derivatives

The present disclosure relates to compositions comprising exendin-4 derivatives and methods for the treatment of hyperinsulinemic hypoglycemia comprising the administration of an exendin-4 derivative to a subject in need thereof. In some embodiments, the exendin-4 derivative is selected from the group consisting of exendin(3-39), exendin(4-39), exendin(5-39), exendin(6-39), exendin(7-39), and exendin (8-39). As used herein, the term "exendin-4 derivative" (e.g., "exendin(3-39)", "exendin(4-39)," "exendin(5-39)," "exendin(6-39)," "exendin(7-39)," and "exendin(8-39)") encompass pharmaceutically acceptable salts of the exendin-4 derivative, including but not limited to sulfate, hydrochloride, phosophate, sulfamate, acetate, citrate, lactate, tartrate, methanesulfonate, ethanesulfonate, benzenesulfonate, p-toluenesulfonate, cyclohexylsulfamate and quinate salts.

In some embodiments, the exendin-4 derivative is exendin(3-39), which is a peptide having the amino acid sequence EGTFTSDL SKQMEEEAVR LFIEWLKNGG PSSGAPPPS (SEQ ID NO:1).

In some embodiments, the exendin-4 derivative is exendin(4-39), which is a peptide having the amino acid sequence GTFTSDL SKQMEEEAVR LFIEWLKNGG PSSGAPPPS (SEQ ID NO:2).

In some embodiments, the exendin-4 derivative is exendin(5-39), which is a peptide having the amino acid sequence TFTSDL SKQMEEEAVR LFIEWLKNGG PSSGAPPPS (SEQ ID NO:3).

In some embodiments, the exendin-4 derivative is exendin(6-39), which is a peptide having the amino acid sequence FTSDL SKQMEEEAVR LFIEWLKNGG PSSGAPPPS (SEQ ID NO:4).

In some embodiments, the exendin-4 derivative is exendin(7-39), which is a peptide having the amino acid sequence TSDL SKQMEEEAVR LFIEWLKNGG PSSGAPPPS (SEQ ID NO:5).

In some embodiments, the exendin-4 derivative is exendin(8-39), which is a peptide having the amino acid sequence SDL SKQMEEEAVR LFIEWLKNGG PSSGAPPPS (SEQ ID NO:6).

In some embodiments, the exendin-4 derivative (e.g., exendin(3-39), exendin(4-39), exendin(5-39), exendin(6-39), exendin(7-39), or exendin(8-39)) is pegylated. In some embodiments, the PEG group has a size of about 5 kD to about 40 kD, e.g., about 20 kD. In some embodiments, the exendin-4 derivative (e.g., exendin(3-39), exendin(4-39), exendin(5-39), exendin(6-39), exendin(7-39), or exendin(8-39)) is pegylated at the N-terminus. In some embodiments, the exendin-4 derivative (e.g., exendin(3-39), exendin(4-39), exendin(5-39), exendin(6-39), exendin(7-39), or exendin(8-39)) is pegylated at the C-terminus. In some embodiments, the PEG is coupled to the exendin-4 derivative via a linker (e.g., a cysteine). Without being bound to a particular theory, it is believed that adding PEG at the N-terminus or C-terminus of an exendin-4 derivative as described herein will not destabilize the alpha helix structure of the exendin-4 derivative or negatively affect binding affinity of the exendin-4 derivative to the GLP-1 receptor. Thus, in some embodiments, pegylation of exendin(3-39), exendin(4-39), exendin(5-39), exendin(6-39), exendin(7-39), or exendin(8-39) can improve the pharmacokinetic profile of the exendin-4 derivative, reducing the dosing frequency in patients, and/or reduce the amount of exendin-4 derivative that is needed for the treatment and prevention of hyperinsulinemic hypoglycemia.

Dosages and Administration

An exendin-4 derivative as described herein (e.g., exendin (3-39), exendin(4-39), exendin(5-39), exendin(6-39), exendin(7-39), or exendin(8-39), or a pegylated form thereof) may be administered at any therapeutically appropriate dose. In some embodiments, the exendin-4 derivative is administered at a dose of about 0.01 mg, about 0.05 mg, about 0.1 mg, about 0.5 mg, about 1 mg, about 2.5 mg, about 5 mg, about 7.5 mg, about 10 mg, about 15 mg, about 20 mg, about 25 mg, about 30 mg, about 35 mg, about 40 mg, about 45 mg, or about 50 mg. In some embodiments, the exendin-4 derivative is administered at a dose in one of the following ranges (all inclusive of the lower and upper values): 0.01-50 mg, 0.01-10 mg, 0.1-50 mg, 0.1-10 mg, 0.1-1 mg, 0.5-50 mg, 0.5-10 mg, 0.5-5 mg, 1-10 mg, 1-20 mg, 2-20 mg, 4-40 mg, 10-75 mg, 20-50 mg, or 20-40 mg. In some embodiments, a therapeutically effective dose of an exendin-4 derivative or range of doses will vary depending upon the needs and physical attributes of the patient. It will be understood by a person of ordinary skill in the art that the doses described herein can be administered at varying concentrations.

In some embodiments, an exendin-4 derivative (e.g., exendin(3-39), exendin(4-39), exendin(5-39), exendin(6-39), exendin(7-39), or exendin(8-39), or a pegylated form thereof) is administered at a dosage or range of doses as described herein twice a day (BID). In some embodiments, the exendin-4 derivative is administered BID at a dose in the range of about 0.01-50 mg, 0.01-10 mg, 0.1-50 mg, 0.1-10 mg, 0.1-1 mg, 0.5-50 mg, 0.5-10 mg, 0.5-5 mg, 1-10 mg, 1-20 mg, 2-20 mg, 4-40 mg, 10-75 mg, 20-50 mg, or 20-40 mg. In some embodiments, the exendin-4 derivative (e.g., exendin(3-39), exendin(4-39), exendin(5-39), exendin(6-39), exendin(7-39), or exendin(8-39), or a pegylated form thereof) is administered at a dosage or range of doses as described herein once a day (QD). In some embodiments, the exendin-4 derivative is administered QD at a dose in the range of about 0.01-50 mg, 0.01-10 mg, 0.1-50 mg, 0.1-10 mg, 0.1-1 mg, 0.5-50 mg, 0.5-10 mg, 0.5-5 mg, 1-10 mg, 1-20 mg, 2-20 mg, 4-40 mg, 10-75 mg, 20-50 mg, or 20-40 mg. The exendin-4 derivative can be administered more often or less often, as appropriate. In some embodiments, the exendin-4 derivative (e.g., exendin(3-39), exendin(4-39), exendin(5-39), exendin(6-39), exendin(7-39), or exendin(8-39), or a pegylated form thereof) is administered once per week (QW) or twice per week (BIW) at a dose in the range of about 0.01-50 mg, 0.01-10 mg, 0.1-50 mg, 0.1-10 mg, 0.1-1 mg, 0.5-50 mg, 0.5-10 mg, 0.5-5 mg, 1-10 mg, 1-20 mg, 2-20 mg, 4-40 mg, 10-75 mg, 20-50 mg, or 20-40 mg.

In some embodiments, the exendin-4 derivative as described herein (e.g., exendin(3-39), exendin(4-39), exendin(5-39), exendin(6-39), exendin(7-39), or exendin(8-39), or a pegylated form thereof) is administered at a total daily dose of about 0.01 mg, about 0.05 mg, about 0.1 mg, about 0.5 mg, about 1 mg, about 2.5 mg, about 5 mg, about 7.5 mg, about 10 mg, about 15 mg, about 20 mg, about 25 mg, about 30 mg, about 35 mg, about 40 mg, about 45 mg, or about 50 mg. In some embodiments, the exendin-4 derivative is administered at a total daily dose in the range of about 0.01-50 mg, about 0.01-10 mg, about 0.1-50 mg, about 0.1-10 mg, about 0.1-1 mg, about 0.5-50 mg, about 0.5-10 mg, about 0.5-5 mg, about 1-10 mg, about 1-20 mg, about 2-20 mg, about 4-40 mg, about 10-75 mg, about 20-50 mg, or about 20-40 mg.

In some embodiments, an exendin-4 derivative (e.g., exendin(3-39), exendin(4-39), exendin(5-39), exendin(6-39), exendin(7-39), or exendin(8-39), or a pegylated form thereof) is administered prior to the administration of a meal. For example, in some embodiments, an exendin-4 derivative is administered within 60-150 minutes (e.g., within 90-120 minutes) prior to morning and evening meals (or before the two main meals of the day, approximately 6 hours or more apart). In some embodiments, an exendin-4 derivative is administered at least one hour prior to the morning meal. In some embodiments, the dosing schedule is semi-independent of mealtimes. For example, the morning dose can be administered on a predetermined schedule relative to the morning meal and the evening dose can be scheduled at a time independent of the time of the evening meal (e.g., about 12 hours after the morning administration without regard to the time of the evening meal). In some embodiments, the dosing schedule is independent of (i.e., not based on, or dictated by) the timing of meals.

In some embodiments, an exendin-4 derivative as described herein is administered via subcutaneous administration (e.g., subcutaneous injection). Sites of injection, include, but are not limited to, injection in the thigh, abdomen, upper arm region, or upper buttock region. In some embodiments, the exendin-4 derivative is subcutaneously administered twice a day (BID). In some embodiments, the exendin-4 derivative is subcutaneously administered once a day (QD). The exendin-4 derivative can be administered more often or less often, as appropriate. In some embodiments, the exendin-4 derivative is subcutaneously administered once per week (QW) or twice per week (BIW).

In some embodiments, an exendin-4 derivative as described herein is administered at a concentration of about 4-50 mg/mL, about 4-40 mg/mL, about 4-35 mg/mL, about 10-50 mg/mL, about 10-40 mg/mL, about 15-50 mg/mL, about 4-25 mg/mL, about 4-20 mg/mL, about 10-25 mg/mL, about 10-20 mg/mL, about 10-18 mg/mL, about 8-16 mg/mL, about 12-20 mg/mL, about 10-15 mg/mL, or about 13-16 mg/mL (e.g., about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, or about 50 mg/mL).

In some embodiments, the dose is administered in a total volume ranging from 0.25-2 ml injectate, e.g., an injection volume ranging from 0.5-1.5 ml or 0.7-1 ml. In some embodiments, the patient self-administers such a dose at least once a day (QD), and often twice a day (BID). In some embodiments, the patients administers such a dose with each meal, it being understood that "with each meal" typically refers to a set period (at least 60 minutes, for example) before a meal, e.g., the first or last meal of the day. In some embodiments, the patient self-administers such a dose once per week (QW) or twice per week (BIW).

Duration of Treatment and Treatment Outcomes

Patients may receive therapy for a predetermined time, an indefinite time, or until an endpoint is reached. Treatment may be continued on a continuous daily or weekly basis for at least two to three months. In some embodiments, therapy is for at least 30 days, at least 60 days, at least 90 days, at least 120 days, at least 150 days, or at least 180 days. In some embodiments, treatment is continued for at least 6 months, at least 7 months, at least 8 months, at least 9 months, at least 10 months, at least 11 months, or at least one year. In other embodiments, treatment is continued for the rest of the patient's life or until administration is no longer effective in maintaining normal plasma glucose levels to provide meaningful therapeutic benefit.

In some embodiments, patients treated according to the methods of the invention exhibit an improvement in one or more symptoms of hypoglycemia, including but not limited to neuroglycopenic symptoms, beta-adrenergic symptoms, or plasma glucose levels.

In some embodiments, treatment in a patient refers to treatment such that the postprandial plasma glucose nadir is maintained above a concentration of approximately 55 mg/dl (3.0 mmol/liter) based upon the Endocrine Society's Clinical Guidelines (*Journal of Clinical Endocrinology & Metabolism*, March 2009, 94(3): 709-728), and symptoms of hypoglycemia are reduced. Ideally, normal plasma glucose concentrations are maintained, with those skilled in the art recognizing that in humans a plasma glucose level of 65 mg/dl or greater is preferred.

In some embodiments, treatment in a patient refers to treatment such that at least a 15% increase in postprandial plasma glucose nadir is achieved relative to baseline (e.g., before the onset of treatment). In some embodiments, treatment in a patient refers to treatment such that for a patient having a postprandial plasma glucose nadir ≤50 mg/dl at baseline (e.g., before the onset of treatment), an increase in postprandial plasma glucose nadir to ≥55 mg/dl is achieved relative to baseline.

Plasma glucose nadir can be measured, for example, by oral glucose tolerance test (OGTT), by meal tolerance test (MTT), or by continuous glucose monitoring (CGM). In some embodiments, treatment in a patient refers to treatment such that a statistically significant decrease in the severity of one or more symptoms of hypoglycemia overall during OGTT, MTT, or CGM and/or of neuroglycopenic symptoms elicited during the glucose "fall" period of OGTT, MTT, or CGM is achieved relative to baseline (e.g., before the onset of treatment).

IV. Compositions and Kits

In another aspect, pharmaceutical compositions for the treatment or prevention of hyperinsulinemic hypoglycemia are provided. In some embodiments, the pharmaceutical composition comprises exendin(3-39), exendin(4-39), exendin(5-39), exendin(6-39), exendin(7-39), or exendin(8-39). In some embodiments, the pharmaceutical composition comprises a pegylated form of exendin(3-39), exendin(4-39), exendin(5-39), exendin(6-39), exendin(7-39), or exendin(8-39).

In some embodiments, the present disclosure provides for pharmaceutical compositions in which the exendin-4 derivative is formulated (e.g., into a preparation for injection) by dissolving, suspending or emulsifying the exendin-4 derivative in an aqueous or non-aqueous solvent, such as vegetable or other similar oils, synthetic aliphatic acid glycerides, esters of higher aliphatic acids or propylene glycol; and optionally, with conventional additives such as solubilizers, isotonic agents, suspending agents, emulsifying agents, stabilizers and preservatives. In some embodiments, an exendin-4 derivative (e.g., pegylated or unpegylated exendin(3-39), exendin(4-39), exendin(5-39), exendin(6-39), exendin (7-39), or exendin(8-39)) is formulated with a pharmaceutically acceptable diluent or carrier that is suitable for subcutaneous administration. Examples of pharmaceutically acceptable diluents or carriers include, but are not limited to, water, saline, and isotonic buffer solutions. In some embodiments the pharmaceutical composition further comprises one or more additional excipients such as preservatives, tonicity-modifying agents, and pH adjustment agents. In some embodiments, the exendin-4 derivative is formulated in normal saline (0.9% saline), and optionally further comprises one or more preservatives, tonicity-modifying agents, and/or pH adjustment agents.

In some embodiments, an exendin-4 derivative as described herein is formulated for immediate release (e.g., immediate subcutaneous release) using art-known methods. In some embodiment, an exendin-4 derivative as described herein is formulated for extended release (e.g., extended subcutaneous release) using art-known methods.

In some embodiments, a pharmaceutical composition comprising an exendin-4 derivative as disclosed herein is formulated as a sterile, preserved isotonic solution in a unit or multi-dose glass vial or ampule for administration with the use of a syringe, similar to the glucagon emergency kit. In some embodiments, a pharmaceutical composition comprising an exendin-4 derivative as disclosed herein is formulated as a sterile, preserved isotonic solution in a glass cartridge pen-injector device. In some embodiments, a pharmaceutical composition comprising an exendin-4 derivative as disclosed herein is formulated as an injectable suspension in a single-dose pen containing exendin(9-39), a diluent, and one or more needles.

In some embodiments, a pharmaceutical composition comprising an exendin-4 derivative as disclosed herein is conveniently packaged, for example, in the form of the dual-chamber pen device provided by the invention, for patients or their care providers to administer therapeutically effective amounts in doses ranging from 0.01-50 mg, e.g., 0.01-10 mg, 0.01-1 mg, 0.1-10 mg, or 0.1-1 mg. In some embodiments, an exendin-4 derivative as described herein is formulated and administered in an injectable pen device that may be pre-programmed to deliver a fixed dosage amount ranging from 0.01-50 mg, e.g., 0.01-10 mg, 0.01-1 mg, 0.1-10 mg, or 0.1-1 mg, depending upon the needs and physical attributes of the patient. Typically, most adult patients (60-100 kg or more) will receive therapeutic benefit from a single dose in the range of 0.01-10 mg, with some achieving full therapeutic effect with 0.1-1 mg. If necessary, dosing may be initiated at lower doses, and maintained if efficacious or alternatively increased stepwise if an enhanced dose response is desired. For especially small patients, for example in the case of children or infants, a dose as low as 0.05 mg or less might be employed. In some instances, for example in the case of altered subcutaneous absorption or metabolism, doses outside of this range may be warranted.

In another aspect, kits for the treatment or prevention of hyperinsulinemic hypoglycemia are provided. In some embodiments, the kit comprises unit dose forms of the exendin-4 derivative, e.g., a sterile, preserved isotonic solution comprising a unit dose of the exendin-4 derivative (e.g., a dose in the range of 0.01 mg to 50 mg, e.g., 0.01-10 mg, 0.01-1 mg, 0.1-10 mg, or 0.1-1 mg). In some embodiments, the kit further comprises one or more delivery devices, e.g., a syringe or an injectable pen device. In some embodiments, a kit comprises a plurality of individual injectable pen devices (e.g., 2, 3, 4, 5, 6, 7, 8, 9, 10 or more pens in a kit). In some embodiments, the kit comprises two or more individual injectable pen devices that are pre-programmed to deliver a fixed dosage amount of an exendin-4 derivative as disclosed herein (e.g., a dose in the range of 0.01 mg to 50 mg, e.g., 0.01-10 mg, 0.01-1 mg, 0.1-10 mg, or 0.1-1 mg). In some embodiments, the kit further comprises instructions for use (e.g., for administering according to a method as described herein).

EXAMPLES

The following examples are provided to illustrate, but not to limit, the claimed invention.

Example 1. Evaluation of Exendin(5-39) and Pegylated Exendin(5-39)

This prophetic example describes a protocol for evaluating the agonistic and antagonistic activities and pharmacokinetic profiles of exendin(5-39) and pegylated exendin(5-39) for human GLP-1 receptor. The exendin(5-39) peptides to be evaluated are as follows:

```
Pegylated Exendin 5-39 (SEQ ID NO: 3):
(PEG)-TFTSDLSKQMEEEAVRLFIEWLKNGGPSSGAPPPS Exendin 5-39 (SEQ ID NO: 3):
TFTSDLSKQMEEEAVRLFIEWLKNGGPSSGAPPPS
```

The exendin(5-39) and pegylated exendin(5-39) peptides are tested for agonistic and antagonistic activities for human GLP-1 receptor in cell culture. Exendin-4 and exendin(9-39) are used as control compounds in the cell culture studies.

GLP-1 receptor binding affinity is tested in in vitro assays using cell lines that express human GLP-1 receptor.

The improvement in pharmacokinetic parameters for exendin(5-39) and pegylated exendin(5-39) is tested in one or more animal models (e.g., in rat). Exendin-4 and exendin (9-39) are used as control compounds.

In some embodiments, exendin(5-39) and pegylated exendin(5-39) exhibits better antagonistic activity without agonistic activity for GLP-1 receptor as compared to exendin (9-39). In some embodiments, the pharmacokinetic profiles that are obtained for exendin(5-39) and pegylated exendin (5-39) support the use of a lower dose as compared to exendin(9-39) (e.g., a dose that is 10× lower than is used for exendin(9-39), and/or support the use of less frequent dosing as compared to exendin(9-39) (e.g., once weekly or twice weekly dosing) in a patient in need thereof.

Example 2. In Vitro Pharmacology Study of Exendin(5-39), Pegylated Exendin(5-39), Exendin(9-39), and Pegylated Exendin(9-39)

This example describes a study that tested the peptides exendin(5-39), pegylated exendin(5-39), exendin(9-39), and pegylated exendin(9-39) in in vitro cellular functional assays.

The agonistic and antagonistic effects of each of the four peptides on the receptor GLP-1 was tested in βTC6 cells, which are cells that endogenously express the mouse GLP-1 receptor, in a cAMP functional assay.

For the agonist assay, exendin(5-39), pegylated exendin (5-39), exendin(9-39), and pegylated exendin(9-39) were dissolved at a concentration of 10 mM in PBS. Cells were incubated with exendin(5-39), pegylated exendin(5-39), exendin(9-39), or pegylated exendin(9-39) for 10 minutes at room temperature. Following the incubation period, the resulting intracellular level of cAMP was measured by homogenous time resolved fluorescence (HTRF). None of the four peptides exhibited agonistic activity on the human GLP-1 receptor.

For the antagonist assay, exendin(5-39), pegylated exendin(5-39), exendin(9-39), and pegylated exendin(9-39) were dissolved at a concentration of 10 mM in PBS; exendin(5-39) and exendin(9-39) were also dissolved at a concentration of 1 mM in DMSO. Cells were stimulated with 0.3 nM glucagon-like peptide 1 (7-37) [GLP-1 (7-37)], a ligand of the GLP-1 receptor, and incubated with exendin(5-39), pegylated exendin(5-39), exendin(9-39), or pegylated exendin(9-39) for 10 minutes at room temperature. Following the incubation period, the resulting intracellular level of cAMP was measured by HTRF. Overall, exendin(5-39) and exendin(9-39) were found to have comparable antagonistic activity on the human GLP-1 receptor. When exendin(5-39) and exendin(9-39) were dissolved in PBS, exendin(5-39) was about 3 times more potent than exendin(9-39) at blocking the human GLP-1 receptor. When exendin(5-39) and exendin(9-39) were dissolved in DMSO, exendin(9-39) was about four times more potent than exendin(5-39) at blocking the human GLP-1 receptor. See Table 1 below. Pegylated exendin(5-39) and pegylated exendin(9-39) did not exhibit significant antagonistic activity on the human GLP-1 receptor.

TABLE 1

| IC$_{50}$ results for GLP-1 antagonist assay | | |
|---|---|---|
| Peptide | IC$_{50}$ | K$_B$ |
| Exendin(9-39) in PBS | 8.9E−08M | 1.7E−08M |
| Exendin(9-39) in DMSO | 1.5E−09M | 2.9E−10M |
| Exendin(5-39) in PBS | 3.1E−08M | 6.1E−09M |
| Exendin(5-39) in DMSO | 6.3E−09M | 1.2E−09M |

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

The inventions have been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group.

What is claimed is:

1. A method of treating hyperinsulinemic hypoglycemia, the method comprising administering an exendin-4 derivative to a patient in need thereof, wherein the exendin-4 derivative is selected from the group consisting of exendin (3-39), exendin(4-39), exendin(5-39), exendin(6-39), exendin(7-39), and exendin(8-39), and wherein the exendin-4 derivative is administered at a dose of 0.01 mg to 50 mg.

2. The method of claim 1, wherein the exendin-4 derivative is exendin(5-39).

3. The method of claim 1, wherein the exendin-4 derivative is pegylated.

4. The method of claim 1, wherein the exendin-4 derivative is subcutaneously administered.

5. The method of claim 1, wherein the patient has previously had bariatric surgery.

6. The method of claim 5, wherein the patient has previously had a bariatric surgery selected from the group consisting of Roux-en Y gastric bypass, vertical sleeve gastrectomy, placement of an endosleeve device, duodenal mucosal resurfacing, partial bypass of the duodenum, vagal nerve blockade, and pyloroplasty.

7. The method of claim 1, wherein the patient has previously had gastrointestinal surgery.

8. The method of claim 1, wherein the patient has congenital hyperinsulinemic hypoglycemia.

9. The method of claim 1, wherein the exendin-4 derivative is administered at a dose of 0.5 mg to 30 mg.

10. The method of claim 1, wherein the exendin-4 derivative is administered at a dose of 0.01 mg to 1 mg.

11. The method of claim 1, wherein the exendin-4 derivative is administered once per day.

12. The method of claim 1, wherein the exendin-4 derivative is administered twice per day.

13. The method of claim 1, wherein the exendin-4 derivative is administered once per week or twice per week.

14. The method of claim 1, wherein the exendin-4 derivative is exendin(5-39) and wherein the exendin(5-39) is subcutaneously administered at a dose of 0.5 mg to 30 mg twice per day (BID).

15. The method of claim 1, wherein the exendin-4 derivative is exendin(5-39) and wherein the exendin(5-39) is subcutaneously administered at a dose of 0.1 mg to 1 mg twice per day (BID).

16. The method of claim 1, wherein the exendin-4 derivative is a pegylated exendin(5-39) and wherein the pegylated exendin(5-39) is subcutaneously administered at a dose of 0.5 mg to 30 mg once per week (QW) or twice per week (BIW).

17. The method of claim 1, wherein the exendin-4 derivative is a pegylated exendin(5-39) and wherein the pegylated exendin(5-39) is subcutaneously administered at a dose of 0.1 mg to 1 mg once per week (QW) or twice per week (BIW).

* * * * *